United States Patent [19]
Lotan

[11] Patent Number: 6,132,747
[45] Date of Patent: Oct. 17, 2000

[54] COMPOSITIONS AND METHODS FOR INHIBITING NEMATOCYST DISCHARGE

[75] Inventor: Amit Lotan, Jordan Valley, Israel

[73] Assignee: Nidaria Technology Ltd., Jordan Valley, Israel

[21] Appl. No.: 08/865,332

[22] Filed: May 29, 1997

[51] Int. Cl.[7] .............................. A01N 25/00; A61K 9/00; A61K 7/00; A61K 7/42
[52] U.S. Cl. ........................... 424/405; 424/59; 424/400; 424/401; 424/677; 424/681; 514/579; 514/651; 514/829; 514/862
[58] Field of Search .................................. 424/400, 401, 424/405, 59, 677–681; 514/579, 657, 862, 829

[56] References Cited

U.S. PATENT DOCUMENTS

| | | | |
|---|---|---|---|
| 4,234,566 | 11/1980 | Packman et al. | 424/47 |
| 4,873,265 | 10/1989 | Blackman | 514/651 |
| 4,929,619 | 5/1990 | Blackman | 514/263 |

FOREIGN PATENT DOCUMENTS

| | | |
|---|---|---|
| 67563/94 | 7/1994 | Australia . |
| 2110534 | 6/1983 | United Kingdom . |
| WO 94/17779 | 8/1994 | WIPO . |

OTHER PUBLICATIONS

Shiomi et al. "Inhibitory effect of anti–infalmmatory agents on cutaneous capillary leakage induced by six marine venoms", (Abstract), Nippon Suisan Gakkaishi, 55 (1), 131–4, 1989.

Salleo et al., "Gadolinium is a powerful blocker of the activation of Nematocytes of *Pelagia noctiluca*" *J. Exp. Biol.* 187:201–206 (1994).

Information regarding Beach–Aid™ from Bethurum R & D, http://www.Bethurum.com, 2 pages total. 1996.

Burnett, "Human injuries following jellyfish stings" *MMJ* (1992) 41(6):509–513.

El–Matbouli et al., "Light and electron microscopic observations on the route of the triactinomyxon–sporoplasm of *Myxobolus cerebralis* from epidermis into rainbow trout cartilage" *J. Fish Biol.* (1995) 46:919–935.

Fenner et al., "First aid treatment of jellyfish stings in Australia" *Med. J. Aust.* (1993) 158:498–501.

Gerke et al., "The spatial distribution of cations in nematocytes of *Hydra vulgaris*" *Hydrobiologica* (1991) 216/217:661–669.

Godknecht et al., "Discharge and mode of action of the tentacular nematocysts of *Anemonia sulcata* (Anthozoa: Cnidaria)" *Marine Biol.* (1988) 100:83–92.

Hartwick et al., "Disarming the box–jellyfish: Nematocyst inhibition in *chironex fleckeri*" *Med. J. Aust.* (1980) 1:15–20.

Heeger et al., "Protection of human skin against jellyfish (*Cyanea capillata*) stings" *Marine Biol.* (1992) 113:669–678.

Hidaka et al., "Effects of cations on the volume and elemental composition of nematocysts isolated from acontia of the sea anemone *Calliactis polypus*" *Biol. Bull.* (1993) 184:97–104.

Holstein et al., "Fibrous mini–collagens in *hydra* nematocysts" *Science* (1994) 265:402–404.

Holstein and Tardent, "An ultrahigh–speed analysis of exocytosis: nematocyst discharge" *Science* (1984) 223:830–833.

Lotan et al., "Life cycle of *Rhopilema nomadica*: a new immigrant scyphomedusan in the Mediterranean" *Marine Biology* (1992) 112:237–242.

Lotan et al., "Synchronization of the life cycle and dispersal pattern of the tropical invader scyphomedusan *Rhopilema nomadica* is temperature dependent" *Mar. Ecol. Prog. Ser.* (1994) 109:59–65.

Lotan et al., "Delivery of a nematocyst toxin" *Nature* (1995) 375:456.

Lotan et al., "Toxin Compartmentation and Delivery in the Cnidaria: The nematocyst's tubule as a multiheaded poisonous arrow" *J. Exp. Zool.* (1996) 275:444–451.

Lotan et al., "Toxinology and ecology of the Mediterranean jellyfish *Rhopilema nomadica*" *Biochem. Aspects of Marine Pharm.* (1996) eds. Lazrovici et al. (Alaken, Inc., Fort Collins, Colorado) pp. 132–144.

Lubbock, "Chemical recognition and nematocyte excitation in a sea anemone" *J. Exp. Bio.* (1979) 83:283–292.

Lubbock et al., "Novel role of calcium in exocytosis: Mechanism of nematocyst discharge as shown by x–ray microanalysis" *Proc. Natl. Acad. Sci. USA* (1981) 78(6):3624–3628.

Lubbock and Amos, "Removal of bound calcium from nematocyst contents causes discharge" *Nature* (1981) 290(5806):500–501.

Mariscal, "Nematocysts" *Coelenterate Biology: Reviews and new perspectives*, eds. Muscatine and Lenhoff (Academic Press, New York, 1974), pp. 129–179.

Russell et al., "Clinical articles seabather's eruption or "sea lice": New findings and clinical implications" Print–out from Florida Atlantic University World Wide Web site (1995) http://www.fau.edu/safe/sea–lice.html, 7 pages total.

Smothers et al., "Molecular evidence that the myxozoan protists are metazoans" *Science* (1994) 265:1719–1721.

Spaulding, "The life cycle of *peachia quinquecapitata*, an anemone parasitic on medusae during its larval development" *Biol. Bull.* (1972) 143:440–453.

(List continued on next page.)

*Primary Examiner*—Shelley A. Dodson
*Assistant Examiner*—Marina Lamm
*Attorney, Agent, or Firm*—Eitan, Pearl, Latzer & Cohen-Zedek

[57] ABSTRACT

Compositions for inhibiting nematocyst or polar capsule discharge are provided in the form of an effective amount of antihistamine or an effective amount of antihistamine and an effective amount of at least one cation. The compositions can be in the form of ointments or can be added to the environment surrounding the nematocysts or polar capsules. Methods of inhibiting nematocyst or polar capsule discharge using the compositions of the invention are also provided.

35 Claims, 2 Drawing Sheets

OTHER PUBLICATIONS

Tardent, "The cnidarian cnidocyte, a high–tec cellular weaponry" *BioEssays* (1995) 17(4):351–362.

Thorington et al., "Control of Cnida discharge: I. Evidence for two classes of chemoreceptor" *Biol. Bull.* (1988) 174:163–171.

Thorington et al., "Control of discharge: Factors affecting discharge of Cnidae" *The Biology of Nematocysts*, Academic Press, Inc. (1988) pp. 233–253.

Tomchik et al., "Clinical perspectives on seabather's eruption, also known as 'sea lice'" *JAMA* (1993) 269(13):1669–1672.

Vaitukaitis, "Production of Antisera with Small Doses of Immunogen: Multiple Intradermal Injections" *Methods in Enzymology*, vol. 73, ed. Larson and Vunkis (Academic Press, New York, 1981), pp. 46–52.

Wasuwat, "Extract of *Ipomoea pes–caprae* (Convolvulaceae) antagonistic to histamine and jelly–fish poison" *Nature* (1970) 225:758.

Watson, "Ultrastructure and cytochemistry of developing nematocysts" *The Biology of Nematocysts*, Academic Press, Inc. (1988) pp. 143–164.

Watson et al., "Cnidocyte mechanoreceptors are tuned to the movements of swimming prey by chemoreceptors" *Science* (1989) 243:1589–1591.

Weber et al., "Nematocysts (stinging capsules of Cnidaria) as Donnan–potential–dominated osmotic systems" *Int. J. Biochem.* (1989) 184:465–476.

Yokoyama et al., "Some biological characteristics of actinosporeans from the oligochaete *Branchiura sowerbyi*" *Dis. aquat. Org.* (1993) 17:223–228.

Yokoyama et al., "Chemoresponse of actinosporean spores of *Myxobolus cultus* to skin mucus of goldfish *Carassius auratus*" *Dis. aquat. Org.* (1995) 21:7–11.

Activation of Marine stinger

Nematocyst discharge (sting) is control by three steps:
A, Chemical secretions of stimulants from the skin (dermis) bind to sensors.
B, Signal from the sensors activate the capsule.
C, High internal pressure is build in the capsule, followed by ejection of the tubule.

Marine sting repellent

Topical lotion formulation can inhibit nematocyt discharge by interfering with nematocyte control at three different sites:
A. Prevent (reduce) secretions of stimulants from the skin (dermis)
B. Chemical inactivation of the sensor.
C. Chemical inactivation of the capsule discharge mechanism.

COMPOSITIONS AND METHODS FOR INHIBITING NEMATOCYST DISCHARGE

TECHNICAL FIELD

This invention is in the field of compositions which repel and prevent the stinging of marine organisms, such as jellyfish. In particular, compositions and methods for inhibiting the discharge of the stinging structure (nematocyst or polar capsule) are provided.

BACKGROUND

Swimmers and divers throughout the world are familiar with the stinging organisms of the oceans such as jellyfish, sea anemone and coral. Jellyfish stings, although seldom fatal, are a major public health problem. Lotan et al. (1992) *Marine Biology* 112:237–242; Lotan et al. (1994) *Marine Ecology Progress Series* 109:59–65. In the summer months, it is estimated that over 500,000 swimmers and divers in the Chesapeake Bay area and 200,00 persons in Florida are stung by jellyfish, mainly by "sea nettles," the common name of *Chrysaora quinquecirrha*. Burnett et al. (1992) *MMJ* 41(6):509–513. Similarly, between the months of March and August, one in four Florida bathers are stung and more than 10,000 persons require emergency medical treatment for pruritic eruptions caused by contact with jellyfish larvae known as "sea lice." Tomchik et al. (1993) *JAMA* 269(13):1669–1672.

The members of the phylum Cnidaria (e.g., jellyfish, sea anemone and coral) and the phylum Myxozoa are all equipped with stinging subcellular organelles, known as nematocysts, cnidocysts, or polar capsules. The nematocysts are located in specialized cells (nematocytes) and consist of a capsule containing a condensed tubule with potent toxins and threads. When nematocysts discharge, the tubule penetrates into its target organism and releases its toxins. The threads arrayed on the tubule enhance the anchoring and attachment of the nematocyst tubule to its target. Thus, nematocysts are involved in target recognition, toxin delivery, infection and attachment.

All members of the phyla Cnidaria and Myxozoa contain nematocysts of varying sizes, shapes and types. Mariscal, pp. 129–178, "Nematocysts" in COELENTERATE BIOLOGY: REVIEWS AND NEW PERSPECTIVES, eds. Muscatine and Lenhoff (Academic Press, New York, 1974). These different types of cnidocysts function in diverse biological roles including capture of prey, toxin delivery, recognition, attachment, adherence and infection. (see, e.g., Tardent (1995); *Bioessays* 17(4):351–362; Lotan et al. (1995) *Nature* 375:456; Lotan et al. (1996) *Expt'l Zool.* 275:444–451; Lotan et al., pp. 132–144, "*Toxicology and ecology and the Mediterranean jellyfish Rhopilema nomadica*" in BIOCHEMICAL ASPECTS OF MARINE PHARMACOLOGY, eds. Lazarovici et al. (Alaken, Inc., Fort Collins, Colorado, 1996); Spaulding (1972) *Biol. Bull.* 143:440–453; Holstein and Tardent (1984) *Science* 223:830–833 and Mariscal, supra. Thus, although best known for their stinging capabilities, nematocytes also play a key role in recognition, attachment and infection. For example, parasites from the phylum Myxozoa use nematocysts (polar capsules) to recognize and infect their hosts. El-Matbouli et al. (1995) *J. Fish Biol.* 46:919–935 and Yokoyama et al. (i995) *Diseases Aquatic Organ.* 21:7–11.

The main body of the nematocyte cell consists of a dense capsule, the nematocyst, within which is a high folded eversible tubule. Discharge (eversion) of this tubule is driven by the build up of a high internal hydrostatic pressure of approximately 150 atmospheres within the capsule. The eversion of the internally folded tubule occurs within 3 microseconds at accelerations of up to 40,000× g, one of the most rapid mechanical events in cell biology.

The nematocyte can be sub-divided into 3 morphological compartments with different functional entities: the capsule lumen and wall, the tubule and the sensory organelles. The capsule wall and lumen are the main components involved in developing the driving force for nematocyst discharge. The tension on the inner capsule wall during nematocyst discharge reaches up to 375 MPa. Holstein (1994) *Science* 265:402–404. The strong capsule wall is highly permeable to water with a pore size of 600 Dalton. Within the resting nematocyst capsule, concentrations of up to 0.5 M of cations such as $Ca^{++}$, $Mg^{++}$ or $K^+$ can be found. (see, e.g., Tardent, supra; Lubbock et al. (1981) *PNAS* 78(6):3624–3628; Godknecht et al. (1988) *Marine Biology* 100:83–92; Lubbock and Amos (1981) *Nature* 290(5806):500–501; Weber (1989) *Int. J. Biochem.* 184:465–476; Hidaka (1993) *Biol. Bull.* 184:97–104 and Gerke (1991) *Hydrobiologia* 216/217:661–669 for discussions of cations and nematocysts). The anionic counterparts are represented by poly-γ-L-glutamatic acid (PGA) in varying degrees of polymerization. During nematocyst discharge, an extreme increase in internal capsule osmotic pressure occurs due to the influx of water. It has been suggested that the influx of water into the capsule is mediated by an internal release of the cations, such as $Ca^{++}$ in sea anemone or $K^+$ in hydra normally combined with PGA. This osmotic pressure is translated into hydrostatic pressure causing the eruption and then evagination of the tubule form the nematocyst capsule (discharge). After the nematocyst discharge the internal cation concentration of the capsule is dissolved into the surrounded fluids.

The second compartment of the nematocyst is a highly condensed eversible tubule. This tubule serves the main role in nematocyte biological function; namely, the interaction or delivery of substances from the cnidarian or myxozoan into its target. The tubule, which is 200–850 μm when elongated, is twisted more than a hundred times around its axis and is packed into the 3–10 μm diameter of the nematocyst. Godknecht & Tardent (1988) *Marine Biol.* 100:83–92. Hollow barbs, arrayed on the inner surface of the tubule, become everted during discharge and play an important role in the penetration and anchoring of the tubule into its prey. Toxins, contained on the outer surface before discharge, are delivered through the barbs after the nematocyst is anchored. Lotan et al. (1995), supra.

The sensory systems of the nematocyte are responsible for the control of nematocyst discharge. Discharge of nematocysts requires both chemical and mechanical stimulation of the sensory organelles. In the sea anemone *Aiptasia pallida*, two classes of chemical receptors have been identified. One type of receptor is triggered by N-acetylated sugars, while the second chemoreceptor is triggered by certain amino acids. Thorington et al. (1988) *Biol Bull.* 174:163–171. The mechanical sensory system is dependent on activation of the chemoreceptors. These mechanoreceptors, however, can be adjusted by the organism, for instance, by tuning them to unique frequency signals emitted by a favored prey.

Certain fish diseases, including whirling disease, are caused by infection with an obligate parasite of the phylum myxozoan. (see e.g., for descriptions of myxozoan, Yokoyama et al. (1993) *Dis. Aquat. Org* 17:223–228; Yokoyama et al. (1995) *Dis. Aquat. Org.* 21:7–11; Smothers et al. (1994) *Science* 265:1719–172; and El-Matbouli et al. (1995) *J. Fish Biology* 46:919–935). These parasites require two hosts, a fish and an aquatic annelid. The stages emerging from each host are infectious only for the other host, however, at each infectious stage, activated polar capsules (nematocyst) release a tubule that penetrates or adheres to the integument of the target. Host recognition is species-specific, indicating that nematocysts serve an important role in recognition of their host (El-Matbouli, supra).

In sum, nematocysts provide an effective method of delivering a substance deep into the target. Because nematocysts are able to penetrate their target so efficiently, it is difficult to remove them, or to treat after the toxin has penetrated. Conventionally, nematocysts stings have been treated with antidotes such as steroids, aluminum sulfate/surfactant and antihistamines. Tomchik, supra. For example, Wasuwat (1970) *Nature* 225:758 describes how Thai fisherman use an extract made from the leaves of Ipomoea pea-caprae as an antidote to jellyfish poison. When the extract was analyzed, it was found to be mildly antihistaminic. The extract exhibits the same effect against jellyfish poison as two commercially prepared antidotes containing antihistamines. In Australia, vinegar is recommended for treatment of lethal box jellyfish stings. Hartwick et al. (1980) *Med J. Aust.* 1:15–20. Vinegar is not recommended for stings by other species. Fenner et al. (1993) *Med J. Aust.* 158:498–501.

Since post-sting treatments for nematocyst stings are often unsatisfactory, the search for ways to prevent nematocyst discharge has been ongoing. The most often prescribed method of preventing jellyfish stings is avoiding any contact with the nematocysts. Tomchik, supra. However, in the case of microscopic larvae, this often means foregoing all ocean activities during the months of high incidence, (e.g., March through August in Florida). It would, therefore, be useful to have a means for inhibiting nematocyst discharge even when contact does occur.

Australian patent application 67563/94 (WO 94/17779) discloses topical hydrodispersion preparations that are reported to be effective in preventing nematocyst discharge as measured by scanning electron microscopy (SEM). The formulations contain inorganic micropigments incorporated into the lipid phase of the hydrodispersion; an optional UV filtering substance and are essentially free of emulsifiers.

Lubbock (1979) *J. Exp. Biol.* 83:283–292 describes how proteinaceous compounds tend to induce a stronger response leading to nematocyst discharge in sea anemones than either polysaccharides or lipids. The authors could determine no simple recognition basis and speculated that the process of nematocyst discharge was complex. Lubbock and Amos, supra, disclose that isolated nematocyst capsules do not discharge in 50 mM $CaCl_2$. The authors report that inhibition of nematocyst discharge occurs only if a solute that could not rapidly penetrate the capsule wall is used, for example, high molecular weight polyethylene glycol. Thus, calcium in the surrounding environment may stabilize nematocysts because it reduces the differential between the calcium concentration outside the capsule and inside the capsule. Normally, the calcium concentration inside the nematocyst capsule is approximately 600 mM. Normal calcium concentration in sea water is around 7 mM, about 100 fold less than inside the capsule. Thus, increasing the calcium concentration outside the capsule to 50 mM reduces the differential to around 10 fold and may be involved in inhibiting nematocyst discharge.

Heeger et al. (1992) *Marine Biology* 113:669–678 tested the ability of three commercially available sunscreen lotions to inhibit jellyfish nematocyst discharge on samples of live human skin. Two of the three lotions were effective at reducing the number of nematocysts discharged. The authors concluded that glycerol and oil components of the lotions could be masking or suppressing the effects of natural stimuli of the skin, however, even the lotion which did not inhibit nematocyst discharge contained these substances. Hartwick et al. (1980) *Med. J. Australia* 1:15–20 report that commercial sting remedies provide do not inhibit nematocyst discharge.

Thorington et al. *Bioll. Bull.* 174:163–171 (1988) describe two classes of nematocyst chemoreceptor. One class of chemoreceptors is specific for N-acetylated sugars, and is unaffected by antihistamines. The second class of chemoreceptors is specific for amino acids and is inhibited by antihistamines. The authors hypothesized that the N-acetylated sugar receptors are the initial trigger for nematocyst discharge and that the antihistamine-affected receptors are probably activated only upon leakage of amino acids from the puncture wound created in the prey by the sugar-triggered nematocyst. It is therefore, unexpected that the present invention has shown that antihistamines alone are effective at inhibiting nematocyst discharge.

The present invention provides a novel composition that effectively inhibits nematocyst discharge. The composition described herein is extremely effective at inhibiting nematocyst discharge when applied topically prior to exposure to nematocysts. In addition, it was the surprising discovery of the inventor that placing antihistamines and cations into the aqueous environment surrounding nematocyst-bearing organisms effectively inhibits nematocyst discharge. Thus, the present invention provides both protection for swimmers, divers and fishermen, as well as protection from nematocyte-facilitated infection in contexts such as fish farms where the surrounding environment can be treated.

DISCLOSURE OF THE INVENTION

In accordance with one embodiment of the present invention, a composition for inhibiting the discharge of nematocysts comprising an effective amount of an antihistamine is provided. The nematocysts may be discharged from organisms selected from the group consisting of Hydrozoa, Anthozoa, Myxozoa and Schyphoza, preferably from the group consisting of Aurelia sp., Pelagia sp., Chrysaora sp., Anthoplaura sp, Rhopilema sp., Physalia sp., Cyanea sp., Linuche sp., Catostylus, Carybdea sp., Chironex sp., Stomolophus sp., Rhiozostoma and Corinactis sp., more preferably from the group consisting of Aurelia aurita, *Corynactic californica, Anthopleura elegantissima, Pelagia noctiluca, Chrysaora quinquecirrha* and Anthoplaura sp The antihistamine is present in a concentration of from about 0.0005% to about 2.0%, preferably from about 0.001% to about 0.2%. The antihistamine can be any antihistamine, preferably diphenhydramine, cimetidine or tripelennamine, more preferably diphenhydramine.

In yet a further embodiment, the composition further comprises at least one cation. The cation can be $Ca^{++}$, $K^+$, $Na^+$, $Mn^{++}$, $Co^{++}$, $Mg^{++}$, or $Fe^{++}$ and is present in a concentration of from about 50 mM to about 1M, preferably from about 50 mM to about 500 mM, more preferably from about 50 mM to about 200 mM.

In another embodiment the composition is incorporated into an ointment base. In a preferred embodiment, the ointment base does not comprise a glycoprotein, and is a lipid or a silicone polymer. In yet a further embodiment, the ointment base further comprises a sunscreen.

In yet a further embodiment of the present invention, a method is provided for inhibiting nematocyst discharge comprising applying to inventive composition to the skin of a subject prior to contact with nematocysts. In another embodiment, a method is provided for inhibiting nematocyst discharge in an environment surrounding the nematocyst.

As will become apparent, preferred features and characteristics of one aspect of the invention are applicable to any other aspect of the invention.

MODES FOR CARRYING OUT THE INVENTION

Figure 1:
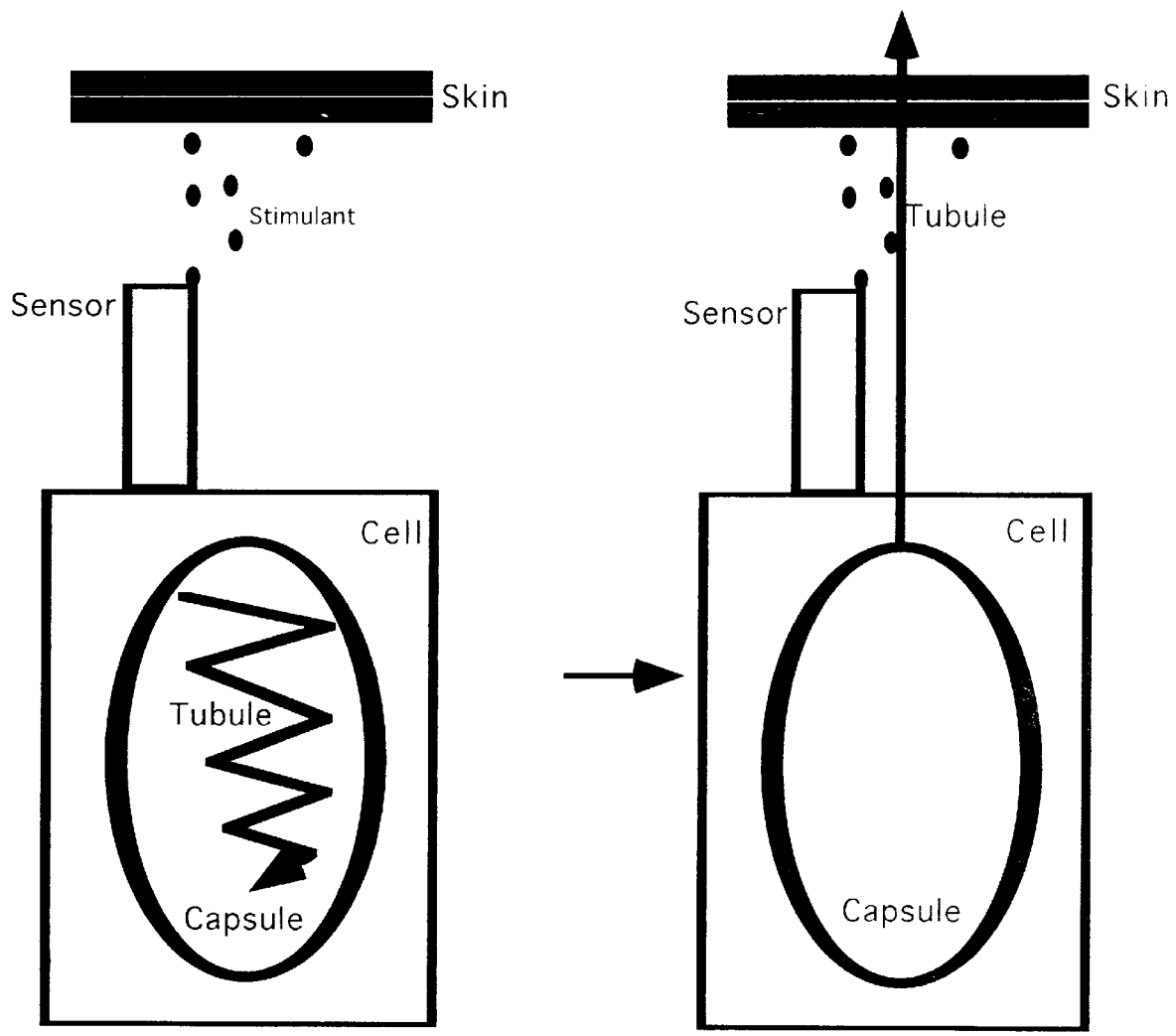
FIG. 1 is a schematic diagram showing three steps activation of nematocysts. Chemical secretions of stimulants from the skin bind to sensors. Signals from the sensors activate the capsule. High internal pressure builds up in the capsule and leads to ejection of the tubule.
Figure 2:
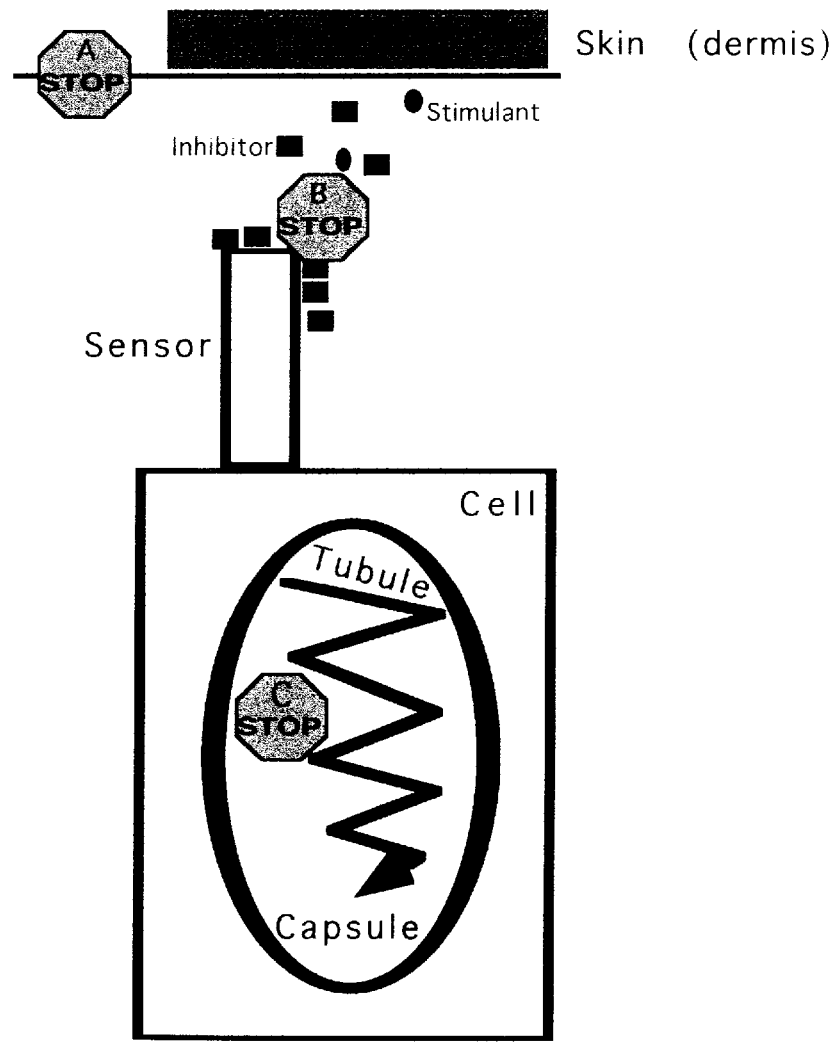
FIG. 2 is a schematic diagram depicting how the formulation will prevent or inhibit discharge of nematocysts. In this depiction, a topical ointment containing the inventive composition is applied to the skin. Secretions of stimulants from the skin are thereby reduced or prevented. The sensors and capsule discharge mechanism are chemically inactivated by the inventive composition.

Throughout this application, various publications, patents, and published patent applications are referred to by an identifying citation. The disclosures of the publications, patents, and published patent specifications referenced in this application are hereby incorporated by reference into the present disclosure to more fully describe the state of the art to which this invention pertains.

As used herein, certain terms will have defined meanings.

The term "nematocyst" or "cnidocyst" or "polar capsule" is used in the conventional sense to refer to the subcellular stinging structures found in the nematocytes or cnidocytes. Nematocysts are described in detail in Tardent, supra and Mariscal, supra. These stinging organelles are capable of penetrating, anchoring into and injecting a substance such as a toxin into a target organism. The terms "nematocyte" or "cnidocyte" or "cnidoblast" are intended to refer to the specialized cell which contain the nematocysts. Non-limiting examples of classes of the phylum Cnidaria which possess cnidocytes include, for example, Hydrozoa, Anthozoa, Myxozoa and Scyphozoa. Examples of jellyfish include, but are not limited to, Aurelia sp., Pelagia sp., Chrysaora sp., Anthoplaura sp., Rhopilema sp., Physalia sp., Cyanea sp., Linuche sp., Catostylus sp., Carybdea sp., Chironex sp., Stomolophus sp., Rhiozostoma sp., Corinactis sp. and the like.

The term "antihistamine" refers to the general class of compounds which inhibit histamine binding. There are generally two types of histamine receptors, $H_1$ and $H_2$. Antagonists of both types of histamine receptors are effective at decreasing or preventing nematocyst discharge.

The term "cation" refers to any positively charged ion. The term "cation source" refers to any substance which is capable of supplying positively charged ions. Preferably, the cations are metal cations. Even more preferably, they are alkali cations, for instance, $Li^+$, $Na^+$ or $K^+$, or alkali earth cations, for instance, $Mg^{++}$, $Ca^{++}$ and the like. Sources of these cations are known to those of skill in the art and are commercially available. Preferably, the source is a salt. Non-limiting examples include $CaCl_2$, $MgCl_2$ and KCl and the like.

The term "ointment base" refers to a vehicle for substances intended for external application to the body. Generally, the base will comprise the main ingredient of a topically applied composition.

The term "glycoprotein" refers to a conjugated protein containing one or more covalently linked carbohydrate residues.

The term "effective amount" refers to an amount sufficient to effect beneficial or desired results. For purposes of this invention, an effective amount of an antihistamine and/or a cation is an amount sufficient to inhibit, limit, repress, palliate or prevent the discharge of nematocysts.

The term "final concentration" refers to the concentration of the ingredient after the composition has been prepared, including, for instance, the concentration of the composition after it has been placed in an aqueous environment.

The term "surrounding environment" refers to the aqueous medium which surrounds stinging marine organisms. It includes, for example, fish ponds, aquariums, ocean enclosures and the like.

The present invention includes chemicals that inhibit nematocyst discharge. Without being bound to one theory, it is believed that the present invention acts to inhibit discharge by interfering with nematocyst discharge at three levels: (1) by reducing secretions of stimulants from the skin; (2) by acting as an antagonist to the chemoreceptor trigger of discharge and (3) by interfering with the build up of hydrostatic pressure required for discharge.

Inhibition of Nematocyst Discharge

The composition of the present invention is effective at inhibiting discharge of nematocysts. In one embodiment, the present invention includes an effective amount of antihistamine and an effective amount of a cation. Preferably, the antihistamine is diphenhydramine, tripelennamine or cimetidine. These antihistamines are commercially available from various suppliers. In the most preferred embodiment, diphenhydramine is used. The antihistamine is added to a final concentration of at least about 0.0005% (or 15 $\mu$M). Preferably, the final concentration is from about 0.0005% to about 2%. More preferably, the concentration is between about 0.001% and about 1%. Even more preferably, the concentration is between about 0.001% and 0.2%. It is believed that higher concentrations of the antihistamine or cations would be effective, but in view of cost considerations and any potential side-effects, the amounts specified above are preferred.

Hydrostatic pressure is the driving force for nematocyst discharge. To generate the needed pressure, bound cations ($Ca^{++}$, $K^+$, $Mg^{++}$, $NH_4^+$, $Na^+$, and/or $Co^{++}$) are released from the internal nematocyst capsule. For example, the $Ca^{++}$ concentration in internal resting nematocysts is 300–600 mM, this $Ca^{++}$ is bound to the PGA matrix. Releasing the $Ca^{++}$ during nematocyst discharge increases the tonicity of the internal capsule and transforms osmotic pressure into hydrostatic pressure. $Ca^{++}$ concentration in the nematocyte cell, outside of the nematocyst capsule, and in sea water is 7 mM. When the $Ca^{++}$ concentration in the surrounding fluids of the capsule reaches 50 mM, the osmolarity of the nematocyst is reduced and discharge is less likely to occur. Because the cations involved in nematocyst discharge may differ between species, the present invention encompasses adding a mixture of cations. In this way, inhibition can be effected for a broader range of species, for example, in both hydra and sea anemones. In another aspect, an effective amount of only one cation is used. Preferably, the cations used are $Ca^{++}$, $K^+$, $Na^{++}$, $Mn^{++}$, $Co^{++}$, $Mg^{++}$, and $Fe^{++}$. Even more preferably, they are $Ca^{++}$, $K^+$ and $Mg^{++}$. These cations can be obtained from various commercial vendors.

Preferably, the concentration of cations is from about 50 mM to about 1 M. More preferably, the concentration is from about 50 mM to about 500 mM. Even more preferably, the concentration is from about 50 mM to about 200 mM. Concentrations greater than 1 M are also likely to be effective. In a preferred embodiment, the cation is included in the ointment base detailed in the following section.

In one aspect, the invention includes adding the compositions described herein to the aqueous environment surrounding the nematocyst-containing organism. An effective amount of the composition is added to the aqueous environment surrounding the nematocysts. The concentrations described above are preferable.

Topical Formulations

In another aspect, the composition of the present invention is formulated for topical application. Preferably, topical formulations containing compositions within the present invention create physical barriers to minimize skin stimulant secretion and, are themselves, not stimulants. Formulations should be water-proof so as to be useful for swimmers and divers. Ca binding compound such as sodium citrate, EDTA, amino acids and glycoproteins generate nematocysts discharge and are, therefore, not to be used. Examples of suitable carriers include, but are not limited to, dextran, dextran sulfate, agarose, phosphatidyl ethanolamine, cholesterol, cholesterol palmitate, palmitic acid, oleic acid, lysolecitin, phosphatidyl choline, phosphatidyl serine, phosphatidyl inositol, squalene, phenyl trimethicone, stearic acid, propylene glycol sterate, petrolatum, stearoxytrimethyl-silane, stearyl alcohol. Other carriers are known to those in the art. Silicone polymers are preferred as they provide good barriers, are water-proof and do not stimulate nematocyst discharge.

Optionally, the compositions described herein may contain a known sunscreen. Preferably, the sunscreens contain at least one UVA filter and at least one UVB filter. Oil-soluble UVB products include 3-benzylidenecamphor derivatives, 4-aminobenzoic acid derivatives, esters of cinnamic acid, derivatives of benzophenone, esters of benzylidenemalonic acid. Water soluble UVA filters include salts of 2-phenylbenzimidazole-5-sulphonic acid, sulphonic acid derivatives of benzophenones and sulphonic acid derivatives of 3-benzylidenecamphor. Effective amounts of sunscreens will be known to those of skill in the art. Preferably, sunscreens will comprise between about 0.1% and 30% by weight of the total preparation.

The following examples are intended to illustrate but not to limit the subject invention.

EXAMPLES

Example 1
Decrease in Nematocyst Discharge Using Antihistamine in the Aqueous Environment To initially test inhibition of nematocyst discharge, the following test was performed. It is typical behavior for jellyfish or sea anemone tentacles to adhere to and paralyze newly hatched nauplii of Artemia sp. The adhesion and subsequent paralysis is characteristic of nematocyst discharge by the tentacles. Small 2 to 3 mm fragments of jellyfish or sea anemone tentacles were prepared and placed in a 12-well plate containing filtered sea water. The tentacle fragments were washed by changing the filtered sea water three times. One mL of filtered sea water was left in each well after the final wash. In 6 of the 12 wells, the antihistamine diphenhydramine hydrochloride was added to final concentration of 0.02%. The 6 wells without the antihistamine served as controls. Ten Artemia sp. were added to each well in a total volume of between 50 and 100 uL of filtered sea water. After 2 minutes, the number of attached or paralyzed Artemia in each well was measured. Results are shown in Table 1.

TABLE 1

| Surrounding water | No. paralyzed Artemia | Total No. Artemia |
| --- | --- | --- |
| sea water + antihistamine | 2 | 10 |
| sea water + antihistamine | 1 | 8 |
| sea water + antihistamine | 2 | 12 |
| sea water + antihistamine | 3 | 14 |
| sea water + antihistamine | 2 | 10 |
| sea water + antihistamine | 1 | 10 |
| sea water alone | 8 | 10 |
| sea water alone | 9 | 13 |
| sea water alone | 9 | 11 |
| sea water alone | 7 | 10 |
| sea water alone | 9 | 11 |
| sea water alone | 8 | 9 |

Taken together, these results show that 11 out of 64 Artemia were paralyzed by nematocysts when antihistamine was added to their environment. In contrast, 50 of 64 Artemia were paralyzed by nematocysts when no antihistamine was present. Diphenhydramine significantly decreased the number of Artemia paralyzed by nematocysts.

Example 2
Inhibition of Nematocyst Discharge onto human skin using Topically applied Antihistamine To test the ability of antihistamines to inhibit nematocyst discharge, an assay using human skin was performed as described herein.

1. Preparation of Skin Samples

Normal human skin (HS) was obtained from neonatal elective circumcision. The skin was immediately placed into sterile phosphate buffered saline (PBS) containing antibiotic/antimycotic. The tissue was frozen embedded in Tissue-Tek™. The tissue was then sectioned into 50 μm sections using a cryostat. The sections were attached to glass slides coated with polylysine and maintained at −70° C. until time of use. All sections were examined to ensure that they were perpendicular to the plane of the epidermis, exposing cross-sections of epidermis, dermis and sub-cutaneous tissue.

2. Immunoassay to detect Nematocyst Discharge

A polyclonal antibody specific for nematocyst toxin was prepared, as described in Lotan et al. (1996), supra. Briefly, the HPLC fraction containing the toxin phospholipase A2 from the jellyfish *Rhopilema nomadica* was isolated and injected into rabbits as described in Vaitukaitis, pp. 46–52, "*Immunochemical techniques*, part B," in METHODS IN ENZYMOLOGY, VOL. 73, ed. Larson & Vunkis (Academic Press, New York, 1981). Serum was collected from the rabbits after two injections, and the presence of toxin examined on immunoblots.

The slides prepared and frozen as described above were thawed at room temperature. The slides were submersed in sea water for approximately 10 seconds and then attached to jellyfish or sea anemones tentacles for approximately 10 seconds. The tentacles were detached, the slides washed two times with PBS, and blocked using 5% Fetal Bovine serum (FBS), and 0.1% Triton X100 in PBS (blocking solution). All washing and incubation steps were conducted on a tilting shaker at room temperature. The slides were incubated in 10 mL of blocking solution containing a 1:2,500 dilution of the anti-toxin antibody for one hour. After incubation, the slides were washed five times for five minutes each wash with 100 mL of 0.1% TritonX100 in PBS (Wash solution). The slides were then incubated in 10 mL blocking solution containing a second antibody, Goat anti rabbit FITC (Fluorescent marker) for 30 minutes. The excess PBS was removed by shaking the slides. One drop of glycerol was added to each slide and the slides covered with a glass coverslip. The slides were observed under a conventional light microscope or under an ultraviolet (UV) microscope at least at 200× magnification.

3. Inhibition of Nematocyst discharge into Human Skin Samples

To monitor nematocyst discharge, three types of live jellyfish, *Aurelia aurita, Pelagia noctiluca*, and *Chrysaora quinquecirrha* and two species of sea anemone, *Anthoplaura elegantissima* and *Corynactis californica* were used in this experiment.

Four frozen human skin slides were thawed at room temperature. Two slides were submersed in glycerol (control) and the other two were submersed in glycerol containing 0.2% diphenhydramine. The slides were placed vertically on a glass dish to allow the glycerol to drip off. The slides were then exposed to one of the jellyfish or sea anemone species noted above and the number of nematocysts discharged was determined using immunohistochemical analysis. On the glycerol only slides, 135 and over 500 nematocysts were counted per slide. On the glycerol plus antihistamine (diphenhydramine) 10 and 52 nematocysts were counted. These results demonstrate that the antihistamine diphenhydramine is effective at inhibiting nematocyst discharge into human skin samples.

To closely parallel the natural conditions under which jellyfish sting humans, the experiment described above was performed at the Monterey Bay Aquarium with the *Chrysaora quinquicirrha* and *Pelagia noctiluca* species of jellyfish. A total of 35 human slides were submersed in control or test substances and exposed to the jellyfish. Six untreated slides, seven slides submersed in glycerol, and seven submersed in glycerol plus 0.2% diphenhydramine were exposed to each jellyfish species for approximately 10 to 15 seconds. The human skin slides exposed to *Chrysaora quinquecirrha* showed that diphenhydramine decreases nematocyst discharge by 2.5–5 fold. In *Pelagia noctiluca* significant reduction in nematocyst discharged was observed. A ten-fold decrease in nematocyst discharge was observed with Aurelia (N=3 for the test and 3 for each control), however, a low number of nematocysts was discharged in the control (less than 100) thus leading to less striking results as compared with those obtained with the other species.

Example 3
Inhibition of Nematocyst Discharge using Antihistamine and Cations

Frozen human skin slides are thawed at room temperature and submersed in glycerol containing 0.2% diphenhydramine and 100 mM $CaCl_2$, KCl or $MgCl_2$. Control slides are submersed in glycerol only. The slides are placed vertically in a glass dish to allow the glycerol to drip off. The slide is then exposed to jellyfish or sea anemone for about 15 seconds. The number of nematocysts that adhere to the skin sample is counted using the procedure described in Example 2.

Example 4
Inhibition of Myxozoan infection

Host recognition and attachment of parasites to their host organisms is effected by nematocyst discharge. For example, the triactinomixon stage of infection recognizes and infects specific fish hosts by extrusion of a polar capsule. Yokoyama, supra. The filaments of the polar capsule penetrate the fish epidermis and anchor the parasites to its host.

To prevent parasitic infections, a final concentration of 0.02% antihistamine diphenhydramine hydrochloride and 100 mM of a cation, e.g., $CaCl_2$, $MgCl_2$, or KCl, is added to the fish pond or aquarium. The cation is selected based on the cation that is normally found in the lumen of the polar capsule. Unlike cnidarian nematocysts, triactinomyxon are exposed to the surrounding environment. Yokoyama, supra have previously shown that the ionic strength of the aqueous environment interferes with the internal structure of the triactinomyxon. Thus, the present invention involves preventing fish infection by two mechanisms: (1) antihistamines to block recognition of the host and (2) cations to inactive the polar capsule.

Fish between 14 and 21 days old that are susceptible to triactinomyxon are exposed to an average of 10,000 waterborne triactinomyxon for approximately 1 hour in a total volume of 100 mL of water. In test aquariums, the water contains 0.02% diphenhydramine hydrochloride and 100 mM KCl, $MgCl_2$ or $CaCl_2$. Control aquariums have no antihistamine or cation. The level of triactinomyxon infection is determined by microscopy, or by immunoassay as described in Example 2. The same concentrations of antihistamine and cation can be used in larger scale fish ponds or aquariums.

I claim:

1. A composition for inhibiting the discharge of nematocysts or polar capsules, the composition comprising an effective amount of an antihistamine and at least one metal cation, wherein the metal cation is $Ca^{++}$, $K^+$, $Na^+$, $Mn^{++}$, $Co^{++}$, $Mg^{++}$ or $Fe^{++}$, in a vehicle suitable for topical application.

2. The composition according to claim 1 wherein the vehicle comprises a lipid.

3. The composition according to claim 1 wherein the vehicle comprises a silicone polymer.

4. The composition according to claim 1 further comprising a sunscreen.

5. The composition of claim 1 wherein the antihistamine is selected from the group consisting of diphenhydramine, cimetidine and tripelennamine.

6. The composition according to claim 1 wherein the antihistamine is diphenhydramine.

7. The composition according to claim 1 wherein the final concentration of the antihistamine is between 0.001% and 0.5%.

8. The composition according to claim 1 wherein the final concentration of the antihistamine is between 0.001% and 0.2%.

9. The composition according to claim 1 wherein the final concentration of the antihistamine is between 0.2% and 0.5%.

10. The composition according to claim 6 wherein the final concentration of diphenhydramine is between 0.001% and 0.5%.

11. The composition according to claim 6 wherein the final concentration of diphenhydramine is between 0.001% and 0.2%.

12. The composition according to claim 6 wherein the final concentration of diphenhydramine is 0.2%.

13. The composition according to claim 1 wherein the nematocysts are discharged from a stinging marine organism selected from the phylum consisting of Cnidaria and Myxozoa.

14. The composition according to claim 1 wherein the cation is $Ca^{++}$.

15. The composition according to claim 1 wherein the cation is $K^+$.

16. The composition according to claim 1 wherein the cation is $Mg^{++}$.

17. The composition according to claim 1 wherein the concentration of the cation is from 50 mM to 1 M.

18. The composition according to claim 1 wherein the concentration of the cation is from 50 mM to 500 mM.

19. The composition according to claim 1 wherein the concentration of the cation is from 50 mM to 200 mM.

20. The composition of claim 19 wherein the cation is at a concentration of 100 mM.

21. A method of inhibiting infection and the toxic effects of nematocyst or polar capsule discharge, comprising applying a composition comprising an antihistamine in a vehicle suitable for topical application, to the skin of a subject prior to contact with nematocysts or polar capsules, thereby inhibiting infection and the toxic effects of nematocyst or polar capsule discharge.

22. The method according to claim 21 wherein the composition further comprises a sunscreen.

23. The method according to claim 21 wherein the antihistamine is selected from the group consisting of diphenhydramine, cimetidine and tripelennamine.

24. The method according to claim 21 wherein the antihistamine is diphenhydramine.

25. The method according to claim 24 wherein the final concentration of diphenhydramine is between 0.001% to 0.2%.

26. The method according to claim 21 wherein the nematocysts are discharged from a stinging marine organism selected from the phylum consisting of Cnidaria and Myxozoa.

27. The method according to claim 26 wherein the stinging marine organism is selected from the group of Cnidaria consisting of jellyfish, sea anemone and coral.

28. The method of claim 21 wherein the composition further comprises at least a metal cation.

29. The method of claim 28 wherein the metal cation is selected from the group consisting of $Ca^{++}$, $K^+$, $Na^+$, $Mn^{++}$, $Co^{++}$, $Mg^{++}$ or $Fe^{++}$.

30. A method of inhibiting infection and the toxic effects of nematocyst or polar capsule discharge, comprising adding an effective amount of an antihistamine to the environment surrounding the nematocyst or polar capsule, thereby inhibiting infection and the toxic effects of nematocyst or polar capsule discharge.

31. The method of claim 30 wherein the antihistamine is at a final concentration of between 0.0005% to 2%.

32. The method according to claim 30 further comprising adding an effective amount of at least one metal cation to the environment surrounding the nematocyst or polar capsule.

33. The method of claim 32 wherein the cation is selected from the group consisting of $Ca^{++}$, $K^+$, $Na^+$, $Mn^{++}$, $Co^{++}$, $Mg^{++}$ or $Fe^{++}$.

34. The method of claim 33 wherein the final concentration of the cation is from 50 mM to 1M.

35. The method of claim 33 wherein the antihistamine is diphenhydramine at a final concentration of 0.02%, and the cation is at a final concentration of 100 mM.

* * * * *